(12) United States Patent
Sturla et al.

(10) Patent No.: US 6,689,340 B1
(45) Date of Patent: *Feb. 10, 2004

(54) HAIR COMPOSITION CONTAINING A POLYCONDENSATE COMPRISING AT LEAST ONE POLYURETHANE AND/OR POLYUREA UNIT AND A POLYOL

(75) Inventors: Jean-Michel Sturla, Boulogne Billancourt (FR); Jean-Luc Bremenson, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/385,009

(22) Filed: Aug. 27, 1999

(30) Foreign Application Priority Data

Aug. 27, 1998 (FR) ............................................. 98 10782

(51) Int. Cl.⁷ ............................ A61K 7/06; A61K 7/11; A61K 7/00; A61K 7/07; A61K 7/09
(52) U.S. Cl. ................... 424/45; 424/70.11; 424/70.12; 424/401; 514/772.1; 514/770; 514/63; 514/880
(58) Field of Search .............................. 424/70.11, 401, 424/45, 70.12; 514/772.1, 63, 770, 880

(56) References Cited

U.S. PATENT DOCUMENTS

| | | | |
|---|---|---|---|
| 4,931,062 A | | 6/1990 | Bay et al. |
| 5,626,840 A | * | 5/1997 | Thomaides et al. ...... 424/70.11 |
| 5,643,581 A | | 7/1997 | Mougin et al. |
| 6,166,093 A | * | 12/2000 | Mougin et al. .......... 514/772.1 |
| 6,495,119 B1 | * | 12/2002 | Sturla et al. ................... 424/45 |

FOREIGN PATENT DOCUMENTS

| | | |
|---|---|---|
| DE | 42 25 045 | 2/1994 |
| DE | 42 41 118 | 6/1994 |
| DE | 43 38 849 | 5/1996 |
| DE | 195 41 326 | 5/1997 |
| EP | 0 542 072 | 5/1993 |
| EP | 0 582 152 | 2/1994 |
| EP | 0 619 111 | 10/1994 |
| EP | 0 636 361 | 2/1995 |
| EP | 0 637 600 | 2/1995 |
| EP | 0 648 485 | 4/1995 |
| EP | 0 656 021 | 6/1995 |
| EP | 0 745 373 | 12/1996 |
| EP | 0 751 162 | 1/1997 |
| EP | 0 756 860 | 2/1997 |
| EP | 0 779 310 | 6/1997 |
| EP | 0 838 211 | 4/1998 |
| EP | 0 838 212 | 4/1998 |
| FR | 2 743 297 | 7/1997 |
| FR | 2 749 568 | 12/1997 |
| WO | WO 93/23009 | 11/1993 |
| WO | WO 94/03510 | 2/1994 |
| WO | WO 96/14049 | 5/1996 |
| WO | WO 96/14050 | 5/1996 |
| WO | WO 97/15275 | 5/1997 |
| WO | WO 97/25021 | 7/1997 |
| WO | WO 98/20833 | 5/1998 |

OTHER PUBLICATIONS

Derwent Publications, Ltd., London, GB; AN 93–410762 (JP 05 310535).
English language Derwent Abstract of DE 42 41 118.
English language Derwent Abstract of DE 4438849.
English language Derwent Abstract of DE 195 41 326.
English language Derwent Abstract of EP 0 636 631.
English language Derwent Abstract of EP 0 637 600.
English language Derwent Abstract of EP 0 648 485.
English language Derwent Abstract of EP 0 745 373.
English language Derwent Abstract of EP 0 751 162.
English language Derwent Abstract of EP 0 756 860.
English language Derwent Abstract of FR 2 743 297.
English language Derwent Abstract of FR 2 749 568.
English language Derwent Abstract of DE 42 25 045.
English language abstract of EP 0 542 072.
English language Derwent Abstract of EP 0 656 021.
English language abstract of EP 0 779 310.

* cited by examiner

Primary Examiner—Frederick Krass
Assistant Examiner—Clinton Ostrup
(74) Attorney, Agent, or Firm—Finnegan, Henderson, Farabow, Garrett & Dunner, LLP

(57) ABSTRACT

The invention relates to hair compositions packaged in aerosol form and comprising, in a cosmetically acceptable medium, a polycondensate, such as a multiblock polymer, comprising at least one polyurethane and/or polyurea unit, at least one polyol, an organic solvent, and a propellant gas. The invention is also directed towards a process for shaping or maintaining the hairstyle, comprising the use of these compositions, as well as to their use for the manufacture of hair products, in order to maintain or shape the hairstyle.

36 Claims, No Drawings

HAIR COMPOSITION CONTAINING A POLYCONDENSATE COMPRISING AT LEAST ONE POLYURETHANE AND/OR POLYUREA UNIT AND A POLYOL

The invention relates to compositions, such as those for hair styling, packaged in aerosol form and comprising, in a cosmetically acceptable medium, a polycondensate, such as a multiblock polymer, comprising at least one polyurethane and/or polyurea unit, at least one polyol, an organic solvent, and a propellant gas. The invention is also directed towards a process for shaping or maintaining a hairstyle comprising the use of these compositions, as well as to their use for the manufacture of hair products, to maintain or shape the hairstyle.

Fixing of the hairstyle is an important element of styling, i.e., maintaining the shape already given or in shaping the hair and fixing it simultaneously.

Hair products for shaping and/or maintaining the hairstyle which are the most common on the cosmetics market are spray compositions comprising a solution, usually an alcoholic or aqueous solution, and one or more materials, generally polymer resins, the function of which is to form welds between the hairs, these materials also being known as fixing materials, as a mixture with various cosmetic adjuvants. This solution can be packaged, for example, in a suitable aerosol container placed under pressure using a propellant. The construction and operation of such aerosol containers is well known to those skilled in the art.

The quality of the spraying obtained by means of an aerosol device, i.e., essentially the distribution of the droplets in space at the nozzle outlet, can depend on the chemical constitution of the composition used and formulations of cosmetic compositions can provide a highly satisfactory spraying quality.

Compositions intended for fixing and/or maintaining the hairstyle sometimes have the drawback of adversely affecting the cosmetic properties of the hair. Thus, the hair can become coarse and lose its natural softness. Styling compositions are thus sought which fix and/or maintain the hairstyle well while at the same time affording good cosmetic properties.

Patent DE 195 41 326 discloses styling compositions distributed from an aerosol device, which contain, in an aqueous-alcoholic medium, a polymer containing polyurethane units as fixing polymer, and a propellant. These compositions, which are already satisfactory in terms of fixing of the hairstyle, can, however, be improved in particular as regards the cosmetic properties which they give to the hair while at the same time offering optimum spraying quality.

The inventors have discovered that combining conditioners with a polycondensate containing at least one polyurethane and/or polyurea unit can satisfy the requirements mentioned above.

The subject of the invention is thus a hair composition, which can be applied to the hair using an aerosol device. In one embodiment, the composition comprises, in a cosmetically acceptable medium, in a relative proportion by weight relative to the total weight of the composition:

(i) 0.1 to 20%, inclusive, of a polycondensate comprising at least one sequence chosen from polyurethanes and polyureas, (ii) 7.5 to 70%, inclusive, of an organic solvent, (iii) 15 to 85%, inclusive, of a propellant gas, and (iv) 0.01 to 20%, inclusive, of at least one polyol, wherein the weight ratio of the propellant gas to the organic solvent is greater than or equal to 1.75:1.

For the purposes of the present invention, the term "polyol" refers to a linear, branched or cyclic, saturated or unsaturated, $C_2$ to $C_{14}$ aliphatic hydrocarbon bearing at least two hydroxyl functional groups, such as on the alkyl chain, as well as polyether polymers of these polyol compounds.

Another subject of the invention relates to a process for shaping or maintaining a hairstyle, comprising the use of the composition of the invention. For example, the composition can be applied to the hair to effect the desired result.

Yet another subject of the invention relates to the use of the composition of the invention for the manufacture of hair compositions, in order to maintain or shape the hairstyle.

Examples of polycondensates comprising at least one polyurethane and/or polyurea compound which are included in the present invention are among the polycondensates described in patents EP 0,751,162, EP 0,637,600, FR 2,743,297 and EP 0,648,485, all assigned to the present assignee, as well as patents EP 0,656,021 and WO 94/03510 from the company BASF, and EP 0,619,111 from the company National Starch. The disclosures of all of these documents are specifically incorporated herein by reference.

The polycondensates used in accordance with the invention can be soluble in a cosmetically acceptable medium, in particular after neutralization with an organic or inorganic base, or alternatively can form a dispersion in this medium. In the latter case, the dispersion can generally comprise at least 0.05% of surfactant, which allows the polycondensate to form a dispersion and to be maintained in dispersion.

According to the invention, any type of surfactant can be used in the dispersion, including a nonionic surfactant. The average size of the polycondensate particles in the dispersion can range from 0.1 to 1 micron (micrometer), inclusive.

By way of example, the polycondensate can be formed by an arrangement of blocks, this arrangement being obtained using:

(1) at least one compound which contains at least two active hydrogen atoms per molecule;

(2) at least one diol containing at least one functional group chosen from acid radicals and salts thereof; and (3) at least one isocyanate chosen from di- and polyisocyanates.

Compound (1) can be chosen from diols, diamines, polyesterols, and polyetherols.

In certain embodiments, compound (1) can be a linear polyethylene or polypropylene glycol, in particular those which are obtained by reaction of ethylene oxide or propylene oxide with water or diethylene or dipropylene glycol in the presence of sodium hydroxide as catalyst. These polyglycols generally have a molecular weight ranging from about 600 to 20,000.

Other suitable organic compounds are those which have mercapto, amino, carboxyl, or hydroxyl groups. Among these, mention may be made more particularly of polyhydroxy compounds such as polyether diols, polyester diols, polyacetal diols, polyamide diols, polyesterpolyamide diols, poly(alkylene ether) diols, polythioether diols, and polycarbonate diols.

Polyether diols can be, for example, the condensation products of ethylene oxide, of propylene oxide, or of tetrahydrofuran, their copolymerization or condensation products, which may be grafted or blocks, such as mixtures of condensates of ethylene oxide and propylene oxide, and the products of polymerization of olefins, at high pressure, with alkylene oxide condensates. Suitable polyethers are prepared, for example, by condensation of alkylene oxides and polyhydric alcohols, such as ethylene glycol, 1,2-propylene glycol and 1,4-butanediol.

The polyester diols, polyesteramides, and polyamide diols can be saturated and are obtained, for example, from the reaction of saturated or unsaturated polycarboxylic acids with polyhydric alcohols, diamines or polyamines. Adipic acid, succinic acid, phthalic acid, terephthalic acid, and maleic acid can be used, for example, to prepare these compounds. Polyhydric alcohols that are suitable for preparing the polyesters include, for example, ethylene glycol, 1,2-propylene glycol, 1,4-butanediol, neopentyl glycol and hexanediol. Amino alcohols, for example ethanolamine, can also be used. Diamines that are suitable for preparing the polyesteramides include, but are not limited to, ethylenediamine and hexamethylenediamine.

Suitable polyacetals can be prepared, for example, from 1,4-butanediol or from hexanediol and from formaldehyde. Suitable polythioethers can be prepared, for example, by condensation reaction between thioglycols, either alone or in combination with other glycols such as ethylene glycol, 1,2-propylene glycol or with other polyhydroxylated compounds. Poly-hydroxylated compounds already containing urea or urethane groups, and natural polyols which can be further modified, for example castor oil and carbohydrates, can also be used.

In certain embodiments, compound (1) is a polyesterol, in particular a polyester diol formed by the reaction of at least one (di)polyol ($1_a$) and at least one acid ($1_b$). The (di)polyol ($1_a$) can be chosen from the group comprising neopentyl glycol, 1,4-butanediol, hexanediol, ethylene glycol, diethylene glycol, propylene glycol, butylene glycol, neopentyl glycol, and (di)polyethylene glycol. The acid ($1_b$) can be chosen from the group comprising phthalic acid, isophthalic acid, adipic acid, and (poly)lactic acid.

A hydroxycarboxylic acid such as dimethylol-propanoic acid (DMPA) or a 2,2-hydroxymethylcarboxylic acid can be used as compound (2). In general, compound (2) is useful as a coupling block. In certain embodiments, compound (2) comprises at least one poly((α-hydroxydiolcarboxylic) acid). In certain other embodiments, compound (2) comprises 2,2-di(hydroxy-methyl)acetic acid, 2,2-dihydroxymethylpropionic acid, 2,2-dihydroxymethylbutyric acid, or 2,2-dihydroxymethylpentanoic acid.

The isocyanate compound (3) can be, but is not necessarily, chosen from hexamethylene diisocyanate, isophorone diisocyanate (IPDI), toluylene diisocyanate, diphenylmethane 4,4'-diisocyanate (DPMD), dicyclohexylmethane 4,4'-diisocyanate (DCMD), methylenebis(p-phenyl) diisocyanate, methylenebis(4-cyclohexyl isocyanate), isophorone diisocyanate, toluene diisocyanate, 1,5-naphthalene diisocyanate, 4,4'-diphenylmethane diisocyanate, 2,2'-dimethyl-4,4'-diphenylmethane diisocyanate, 1,3-phenylene diisocyanate, 1,4-phenylene diisocyanate, mixtures of 2,4- and 2,6-toluene diisocyanate, 2,2'-dichloro-4,4'-diisocyanatodiphenylmethane, 2,4-dibromo-1,5-diisocyanatonaphthalene, butane 1,4-diisocyanate, 1,6-hexane diisocyanate, and 1,4-cyclohexane diisocyanate.

The polycondensate can be formed using at least one additional compound (4), which generally serves to extend the polycondensate chain. Examples of compounds suitable as compound (4) include, but are not limited to, saturated or unsaturated glycols such as ethylene glycol, diethylene glycol, neopentyl glycol or triethylene glycol; amino alcohols such as ethanolamine, propanolamine, or butanolamine; heterocyclic, aromatic, cycloaliphatic, and aliphatic primary amines; diamines; carboxylic acids such as aliphatic, aromatic, or heterocyclic carboxylic acids, for instance oxalic acid, succinic acid, glutaric acid, adipic acid, sebacic acid, or terephthalic acid; and amino carboxylic acids. In certain embodiments, compound (4) is an aliphatic diol.

The polycondensates in accordance with the invention can also be formed from at least one additional compound (5), having a silicone skeleton. In certain embodiments, compound (5) is chosen from polyethylsiloxanes, polymethylsiloxanes, and polyphenylsiloxanes. In embodiments, compound (5) optionally contains hydrocarbon-based chains grafted onto at least one silicon atom. In certain embodiments, the polyalkylsiloxane is chosen from polyethylsiloxanes and polymethylsiloxanes, and the polyarylsiloxane is chosen from polyphenylsiloxanes.

According to an embodiment of the compositions in accordance with the invention, the sequence(s) chosen from polyurethanes and polyureas have a repeating base unit corresponding to the formula (I):

$$—X—B—X—CO—NH—R—NH—CO— \quad (I)$$

in which:

X is chosen from O and NH,

B is a divalent hydrocarbon-based radical, this radical being substituted or unsubstituted, and R is a divalent substituted or unsubstituted radical chosen from aromatic alkylene radicals, $C_1$ to $C_{20}$ aliphatic radicals, and $C_1$ to $C_{20}$ cycloaliphatic radicals.

In certain embodiments, radical B is a $C_1$ to $C_{30}$ divalent hydrocarbon-based radical and bears a group containing one or more carboxylic functional groups and/or one or more sulphonic functional groups. In these embodiments, the carboxylic and/or sulphonic functional groups are in free form or else partially or totally neutralized with an inorganic or organic base.

Radical R can be chosen from radicals corresponding to the following formulae:

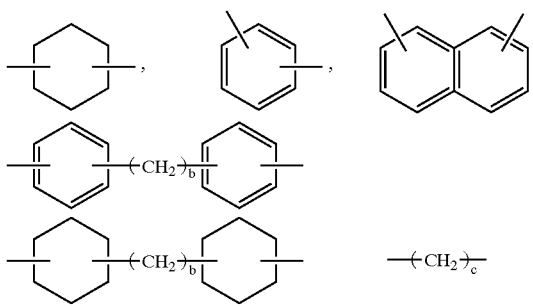

in which b is an integer ranging from 0 to 3, inclusive, and c is an integer ranging from 1 to 20, inclusive, such as ranging from 2 to 12, inclusive.

In certain embodiments, radical R is chosen from hexamethylene, 4,4'-biphenylenemethane, 2,4- and/or 2,6-tolylene, 1,5-naphthylene, p-phenylene and methylene-4,4-bis-cyclohexyl radicals, and divalent radicals derived from isophorone.

The polycondensate used in accordance with the invention comprising at least one polyurethane and/or polyurea compound can also comprise at least one polysiloxane compound in which the repeating base unit corresponds, for example, to the formula (II):

$$—X—P—X—CO—NH—R—NH—CO— \quad (II)$$

in which:

P is a polysiloxane segment,

X is chosen from O and NH, and

R is chosen from divalent substituted or unsubstituted radicals chosen from aromatic alkylene radicals, $C_1$ to $C_{20}$ aliphatic radicals, and $C_1$ to $C_{20}$ cycloaliphatic radicals.

In certain embodiments, the polysiloxane segment P corresponds to the formula (III):

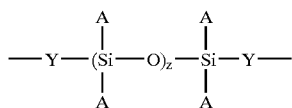

(III)

in which:

the radicals A, which can be identical or different, are chosen from, on the one hand, $C_1$ to $C_{20}$ monovalent hydrocarbon-based radicals which are free or substantially free of ethylenic unsaturation and, on the other hand, aromatic radicals, Y represents a divalent hydrocarbon-based radical, and z represents an integer chosen such that the average molecular weight of the polysiloxane segment ranges from 300 to 10,000.

In general, the divalent radical Y is chosen from alkylene radicals of formula $—(CH_2)_a—$, in which a represents an integer which can range from 1 to 10.

The radicals A can be, but are not necessarily, chosen from alkyl radicals, such as methyl, ethyl, propyl, isopropyl, butyl, pentyl, hexyl, octyl, decyl, dodecyl and octadecyl radicals; cycloalkyl radicals, such as the cyclohexyl radical; aryl radicals, including phenyl and naphthyl; arylalkyl radicals, such as benzyl and phenylethyl; and tolyl and xylyl radicals.

The composition in accordance with the invention can generally comprise, in a relative proportion by weight relative to the total weight of the composition, between 0.1 and 20%, inclusive, of the polycondensate comprising at least one sequence chosen from polyurethanes and polyureas. In embodiments, the composition comprises between 1 and 15%, inclusive, of the polycondensate, by weight of the total weight of the composition. In embodiments, the composition comprises between 2 and 8%, inclusive, of the polycondensate, by weight of the total weight of the composition.

An organic solvent can generally make up between 7.5 and 70%, inclusive, of the total weight of the composition. In certain embodiments, the composition comprises between 10 and 50%, inclusive, of said organic solvent, by weight of the total weight of the composition. In certain embodiments, the composition comprises between 10 and 25%, inclusive, of the organic solvent, by weight of the total weight of the composition. In accordance with the invention, the organic solvent can be, but is not necessarily, chosen from the group comprising $C_1$ to $C_4$ lower alcohols such as ethanol and isopropanol; acetone; methyl ethyl ketone; methyl acetate; butyl acetate; ethyl acetate; dimethoxyethane; diethoxyethane; and mixtures thereof. For example, in certain embodiments, ethanol is used.

Certain embodiments of the composition of the invention comprise a propellant gas. In these embodiments, the composition can generally comprise, by weight, between 15 and 85%, inclusive, of the propellant gas. In certain embodiments, the composition comprises between 25 and 60%, inclusive, of the propellant gas, by weight of the total weight of the composition. In certain other embodiments, the composition comprises between 30 and 50%, inclusive, of the propellant gas, by weight of the total weight of the composition.

In accordance with the invention, a gas which is soluble or insoluble in the composition, such as dimethyl ether, fluoro or non-fluoro hydrocarbons, the usual liquefied gases used as propellants in body-treating compositions, or a mixture of these propellant gases is used as propellant gas. For example, dimethyl ether can be used.

The composition of the invention can comprise at least one polyol or a mixture of polyols. The relative proportion by weight, relative to the total weight of the composition, of polyol or of a mixture of polyols can generally be between 0.01 and 20%, inclusive. In certain embodiments, the composition comprises between 0.01 and 10%, inclusive, of at least one polyol, by weight of the total weight of the composition. In certain other embodiments, the composition comprises between 0.05 and 5%, inclusive, of at least one polyol, by weight of the total weight of the composition.

The polyols used according to the invention can be, but are not necessarily, chosen from $C_2$ to $C_{14}$ saturated and unsaturated, linear, branched, and cyclic aliphatic hydrocarbon compounds bearing at least two hydroxyl functions on the alkyl chain, and polyether polymers of at least one polyhydroxyalkyl compound. The polyols used according to the invention can be, but are not necessarily, chosen from polyalkylene glycols such as polyethylene glycols and polypropylene glycols. In certain embodiments, a $C_2$ to $C_{12}$ or $C_2$ to $C_8$ polyhydroxyalkane derivative is used as polyol. A $C_3$ to $C_5$ compound can be chosen, including, but not limited to, glycerol, propylene glycol, or 1,3-propanediol.

The compositions in accordance with the invention can moreover contain at least one cosmetic additive. The additive(s) can be chosen from fatty substances, thickeners, softeners, antifoaming agents, moisturizers, antiperspirants, basifying agents, dyes, pigments, fragrances, preserving agents, surfactants, hydrocarbon-based polymers, volatile and non-volatile silicones, proteins, and vitamins. In certain embodiments, the additive is chosen from anionic silicones.

In accordance with certain embodiments of the invention, cosmetic compositions are prepared in which the amount of expelled volatile organic compounds is increasingly small. In particular, the polyurethane of the invention can be combined with at least one other nonionic, anionic, cationic, or amphoteric fixing polymer.

A better understanding of the invention may be gained with the aid of the non-limiting example which follows and which constitutes an embodiment of the compositions in accordance with the invention.

EXAMPLE

The following hair composition in accordance with the invention is prepared.

Lactic acid polyester/ethylene glycol P(PMIS-EG)-dimethylol propanoic acid (DMPA)-isophorone diisocyanate polycondensate; . . . 4 g Glycero . . . 0.07 g Ethanol . . . 15 g Dimethyl ether . . . 35 g 2-Amino-2-methyl-1-propanol . . . qs neutralization Demineralized water . . . qs 100 g

What is claimed is:

1. A composition for application to the hair using an aerosol device, said hair composition comprising in a relative proportion by weight relative to the total weight of the composition:

(i) 0.1 to 20%, inclusive, of a polycondensate comprising at least one sequence chosen from polyurethanes and polyureas, (ii) 7.5 to 70%, inclusive, of an organic solvent, (iii) 15 to 85%, inclusive, of a propellant gas, and (iv) 0.01 to 20%, inclusive, of at least one polyol, wherein the weight ratio of the propellant gas to the organic solvent is greater than or equal to 1.75:1.

2. The composition according to claim 1, wherein the polycondensate is formed by an arrangement of blocks obtained using:

(1) at least one compound which contains at least two active hydrogen atoms per molecule;

(2) at least one diol containing at least one functional group chosen from acid radicals and salts thereof; and (3) at least one isocyanate chosen from di- and polyisocyanates.

3. The composition according to claim 2, wherein said at least one compound (1) is chosen from diols, diamines, polyesterols, and polyetherols.

4. The composition according to claim 2, wherein said at least one diol (2) is a 2,2-hydroxymethyl carboxylic acid.

5. The composition according to claim 2, wherein said at least one isocyanate (3) is chosen from hexamethylene diisocyanate, isophorone diisocyanate, toluylene diisocyanate, diphenylmethane 4,4'-diisocyanate dicyclohexylmethane 4,4'-diisocyanate, methylenebis(p-phenyl) diisocyanate, methylenebis(4-cyclohexyl isocyanate), isophorone diisocyanate, toluene diisocyanate, 1,5-naphthalene diisocyanate, 4,4'-diphenylmethane diisocyanate, 2,2'-dimethyl-4,4'-diphenylmethane diisocyanate, 1,3-phenylene diisocyanate, 1,4-phenylene diisocyanate, mixtures of 2,4- and 2,6-toluene diisocyanate, 2,2'-dichloro-4,4'-diisocyanatodiphenylmethane, 2,4-dibromo-1,5-diisocyanatonaphthalene, butane 1,4-diisocyanate, 1,6-hexane diisocyanate, and 1,4-cyclohexane diisocyanate.

6. The composition according to claim 2, wherein the polycondensate is formed from at least one additional compound having a silicone skeleton.

7. The composition according to claim 6, wherein the at least one additional compound having a silicone skeleton is chosen from polysiloxanes, polyalkylsiloxanes, and polyarylsiloxanes, and wherein said polysiloxanes, polyalkylsiloxanes, and polyarylsiloxanes optionally contain hydrocarbon-based chains grafted onto at least one silicone atom.

8. The composition according to claim 7, wherein the polyalkylsiloxane is chosen from polyethylsiloxanes and polymethylsiloxanes, and the polyarylsiloxane is chosen from polyphenylsiloxanes.

9. The composition according to claim 1, wherein said at least one sequence chosen from polyurethanes and polyureas has a repeating base unit corresponding to the formula (I):

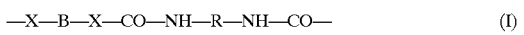

in which:

X is chosen from O and NH,

B is a divalent hydrocarbon-based radical, this radical being substituted or unsubstituted, and R is a divalent substituted or unsubstituted radical chosen from aromatic alkylene radicals, $C_1$ to $C_{20}$ aliphatic radicals, and $C_1$ to $C_{20}$ cycloaliphatic radicals.

10. The composition according to claim 9, wherein B is a $C_1$ to $C_{30}$ divalent hydrocarbon-based radical.

11. The composition according to claim 9, wherein radical R is chosen from hexamethylene, 4,4'-biphenylenemethane, 2,4-tolylene, 2,6-tolylene, 1,5-naphthylene, p-phenylene-4, 4-bis-cyclohexyl radicals, methylene-4,4-bis-cyclohexyl radicals, and divalent radicals derived from isophorone.

12. The composition according to claim 1, wherein the polycondensate has a repeating base unit corresponding to formula (II):

in which:

P is a polysiloxane segment,

X is chosen from O and NH, and

R is chosen from divalent substituted and unsubstituted radicals chosen from aromatic alkylene radicals, $C_1$ to $C_{20}$ aliphatic radicals, and $C_1$ to $C_{20}$ cycloaliphatic radicals.

13. The composition according to claim 1, comprising between 1 and 15%, inclusive, of said polycondensate, by weight of the total weight of the composition.

14. The composition according to claim 13, comprising between 2 and 8%, inclusive, of said polycondensate, by weight of the total weight of the composition.

15. The composition according to claim 1, comprising between 10 and 50%, inclusive, of said organic solvent, by weight of the total weight of the composition.

16. The composition according to claim 15, comprising between 10 and 25%, inclusive, of said organic solvent, by weight of the total weight of the composition.

17. The composition according to claim 1, comprising between 25 and 60%, inclusive, of said propellant gas, by weight of the total weight of the composition.

18. The composition according to claim 17, comprising between 30 and 50%, inclusive, of said propellant gas, by weight of the total weight of the composition.

19. The composition according to claim 1, comprising between 0.01 and 10%, inclusive, of said at least one polyol, by weight of the total weight of the composition.

20. The composition according to claim 19, comprising between 0.05 and 5%, inclusive, of at said least one polyol, by weight of the total weight of the composition.

21. The composition according to claim 1, wherein said at least one polyol is chosen from $C_2$ to $C_{14}$ saturated and unsaturated, linear, branched and cyclic aliphatic hydrocarbon compounds bearing at least two hydroxyl functions on the alkyl chain and polyether polymers of at least one polyhydroxyalkyl compound.

22. The composition according to claim 21, wherein said at least one polyol is chosen from $C_2$ to $C_{12}$ polyhydroxalkane derivatives.

23. The composition according to claim 21, wherein said at least one polyol is chosen from $C_2$ to $C_8$ polyhydroxalkane derivatives.

24. The composition according to claim 21, wherein said at least one polyol is chosen from $C_3$ to $C_5$ polyhydroxyalkane derivatives.

25. The composition according to claim 1, further comprising at least one cosmetic additive.

26. The composition according to claim 25, wherein the at least one cosmetic additive is chosen from fatty substances, thickeners, softeners, antifoaming agents, moisturizers, antiperspirants, basifying agents, dyes, pigments, fragrances, preserving agents, surfactants, hydrocarbon-based polymers, and volatile and non-volatile silicones, polyols, proteins, and vitamins.

27. The composition according to claim 25, wherein the at least one additive is chosen from anionic silicones.

28. The composition according to claim 1, further comprising at least one fixing polymer.

29. The composition according to claim 28, wherein said at least one fixing polymer is chosen from nonionic, cationic, anionic, and amphoteric fixing polymers.

30. A composition comprising:
a) lactic acid polyester/ethylene glycol P(PMIS-EG)-dimethylol propanoic acid (DMPA)-isophorone diisocyanate polycondensate;
b) glycerol;
c) ethanol;
d) dimethyl ether;
e) 2-amino-2-methyl-1-propanol; and
f) demineralized water.

31. The composition of claim 30, comprising:
a) 4% by weight, lactic acid polyester/ethylene glycol P(PMIS-EG)-dimethylol propanoic acid (DMPA)-isophorone diisocyanate polycondensate;
b) 0.07% by weight, glycerol;
c) 15% by weight, ethanol;
d) 35% by weight, dimethyl ether;
e) a sufficient amount of 2-amino-2-methyl-1-propanol to neutralize the composition; and
f) a sufficient amount of demineralized water to raise the total weight to 100%.

32. An aerosol device comprising a container containing a composition comprising in a relative proportion by weight relative to the total weight of the composition:
(i) 0.1 to 20%, inclusive, of a polycondensate comprising at least one sequence chosen from polyurethanes and polyureas,
(ii) 7.5 to 70%, inclusive, of an organic solvent,
(iii) 15 to 85%, inclusive, of a propellant gas, and
(iv) 0.01 to 20%, inclusive, of at least one polyol or a mixture thereof,
wherein the weight ratio of the propellant gas to the organic solvent is greater than or equal to 1.75:1.

33. The device of claim 32, comprising a means for distributing the composition.

34. A process for shaping or maintaining a hairstyle, said process comprising applying to hair, using an aerosol device, a composition comprising in a relative proportion by weight, relative to the total weight of the composition:
(i) 0.1 to 20%, inclusive, of a polycondensate comprising at least one sequence chosen from polyurethanes and polyureas,
(ii) 7.5% to 70%, inclusive, of an organic solvent,
(iii) 15 to 85%, inclusive, of a propellant gas, and
(iv) 0.01 to 20%, inclusive, of at least one polyol or a mixture thereof,
wherein the weight ratio of the propellant gas to the organic solvent is greater than or equal to 1.75:1.

35. A process of manufacturing a hair product for maintaining or shaping a hairstyle, said process comprising including in said hair product a composition, applied to hair using an aerosol device, comprising in a relative proportion by weight, relative to the total weight of the composition:
(i) 0.1 to 20%, inclusive, of a polycondensate comprising at least one sequence chosen from polyurethanes and polyureas,
(ii) 7.5% to 70%, inclusive, of an organic solvent,
(iii) 15 to 85%, inclusive, of a propellant gas, and
(iv) 0.01 to 20%, inclusive, of at least one polyol or a mixture thereof,
wherein the weight ratio of the propellant gas to the organic solvent is greater than or equal to 1.75:1.

36. The process of claim 35, further comprising the placing the hair product in a container suitable for delivering said composition to hair.

* * * * *

UNITED STATES PATENT AND TRADEMARK OFFICE
CERTIFICATE OF CORRECTION

PATENT NO. : 6,689,340 B1
DATED : February 10, 2004
INVENTOR(S) : Jean-Michel Sturla et al.

It is certified that error appears in the above-identified patent and that said Letters Patent is hereby corrected as shown below:

<u>Column 8,</u>
Line 38, "at said least" should read -- said at least --.
Lines 47 and 48, "polyhydroxalkane" should read -- polyhydroxyalkane --.
Lines 50 and 51, "polyhydroxalkane" should read -- polyhydroxyalkane --.

Signed and Sealed this

Sixth Day of July, 2004

JON W. DUDAS
*Acting Director of the United States Patent and Trademark Office*